(12) United States Patent
Hoffman

(10) Patent No.: US 10,695,902 B2
(45) Date of Patent: Jun. 30, 2020

(54) PHARMACY ORDER PROCESSING SYSTEM

(71) Applicant: Express Scripts Strategic Development, Inc., St. Louis, MO (US)

(72) Inventor: Robert E. Hoffman, Linden, IN (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 57 days.

(21) Appl. No.: 15/996,909

(22) Filed: Jun. 4, 2018

(65) Prior Publication Data
US 2019/0367275 A1 Dec. 5, 2019

(51) Int. Cl.
| | |
|---|---|
| B25J 9/00 | (2006.01) |
| B25J 9/16 | (2006.01) |
| B25J 9/02 | (2006.01) |
| B65G 1/137 | (2006.01) |
| G16H 20/13 | (2018.01) |
| G05B 15/02 | (2006.01) |
| B25J 18/04 | (2006.01) |

(52) U.S. Cl.
CPC ......... *B25J 9/0096* (2013.01); *B25J 9/0093* (2013.01); *B25J 9/02* (2013.01); *B25J 9/1679* (2013.01); *B25J 18/04* (2013.01); *B65G 1/1373* (2013.01); *G05B 15/02* (2013.01); *G16H 20/13* (2018.01); *B65G 2201/0235* (2013.01)

(58) Field of Classification Search
CPC .................................................. B25J 9/0096
See application file for complete search history.

(56) References Cited

U.S. PATENT DOCUMENTS

| | | | | |
|---|---|---|---|---|
| 4,944,647 A | * | 7/1990 | Oleson | ............... B65B 69/0033 |
| | | | | 198/417 |
| 5,720,154 A | | 2/1998 | Lasher et al. | |
| 5,771,657 A | | 6/1998 | Lasher et al. | |
| 6,026,561 A | * | 2/2000 | Lafond | ............. H01L 21/67778 |
| | | | | 29/722 |
| 6,769,228 B1 | | 8/2004 | Mahar | |
| 6,892,512 B2 | | 5/2005 | Rice et al. | |
| 7,185,477 B2 | | 3/2007 | Rice et al. | |
| 7,530,211 B2 | * | 5/2009 | McErlean | ............... B65B 5/103 |
| | | | | 414/403 |
| 7,765,776 B1 | | 8/2010 | Leu et al. | |
| 8,117,809 B2 | * | 2/2012 | McErlean | ............... B65B 5/103 |
| | | | | 414/403 |

(Continued)

*Primary Examiner* — Thomas Randazzo
(74) *Attorney, Agent, or Firm* — Stinson LLP

(57) ABSTRACT

A pharmacy order processing system includes a container disassembly workstation defining a container disassembly workspace and a bulk container area including a plurality of bulk containers configured to receive a plurality of pharmaceuticals. The container disassembly workstation includes a holding area, a cutter device, a container manipulation device, a pharmaceutical receptacle, and a container receptacle. The cutter device includes a cutter head and is configured to cut through at least one wall of at least one container to separate at least a first portion of the at least one container of the plurality of containers from a second portion of the at least one container when the at least one container is in a cutter position. The container manipulation includes a gripper device and is configured to move the at least one container between at least the holding position and the cutter position within the container disassembly workspace.

30 Claims, 10 Drawing Sheets

(56) References Cited

U.S. PATENT DOCUMENTS

| | | | |
|---|---|---|---|
| 8,539,742 B2* | 9/2013 | McErlean | B65B 5/103 |
| | | | 414/403 |
| 8,600,903 B2 | 12/2013 | Eller | |
| 9,242,751 B1 | 1/2016 | Joplin et al. | |
| 9,567,119 B2 | 2/2017 | Joplin | |
| 9,639,668 B2 | 5/2017 | Joplin | |
| 2004/0090153 A1 | 5/2004 | Touzani | |
| 2004/0123567 A1* | 7/2004 | McErlean | B65B 5/103 |
| | | | 53/445 |
| 2005/0279745 A1 | 12/2005 | Gupta | |
| 2006/0162298 A1 | 7/2006 | Oh et al. | |
| 2010/0258565 A1* | 10/2010 | Isaacson | B09B 3/0075 |
| | | | 220/324 |
| 2012/0109081 A1* | 5/2012 | Romano | A61M 1/0001 |
| | | | 604/290 |
| 2018/0144285 A1 | 5/2018 | Hoffman et al. | |
| 2019/0126331 A1* | 5/2019 | VanderWoude | A61M 5/3205 |

* cited by examiner

312 — PLACING THE FIRST PORTION OF THE AT LEAST ONE CONTAINER AND THE SECOND PORTION OF THE AT LEAST ONE CONTAINER IN A CONTAINER RECEPTACLE, WHEREIN THE CONTAINER RECEPTACLE DEFINES AN OPENING SIZED TO RECEIVE THE FIRST PORTION OF THE AT LEAST ONE CONTAINER AND THE SECOND PORTION OF THE AT LEAST ONE CONTAINER

PHARMACY ORDER PROCESSING SYSTEM

FIELD

The present disclosure relates generally to the technical field of pharmacy order processing, and more particularly, to methods and systems for removing pharmaceuticals from relatively small volume pharmaceutical containers and transferring the removed pharmaceuticals to relatively larger volume pharmaceutical containers, especially in a high volume, specialty, or partially-automated order processing center.

BACKGROUND

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Pharmaceutical order processing systems typically involve labor intensive processes to remove pharmaceuticals from manufacturer packaging, transfer the pharmaceuticals to a bulk storage container, retrieve the pharmaceuticals, and fill and package the many pharmacy orders. Many of the pharmacy orders are custom or specialty orders that require a quantity of specific pharmaceuticals that necessitates emptying multiple original manufacturer containers to fill a single order, and thus the process for filling the orders is difficult to efficiently complete and requires substantial operator interaction throughout the process. Improved systems and methods for filling custom or specialty pharmacy orders at a high volume to improve order fulfillment realization and customer satisfaction are needed.

BRIEF SUMMARY

In one aspect, a pharmacy order processing system includes a container disassembly workstation defining a container disassembly workspace and a bulk container area including a plurality of bulk containers. The container disassembly workstation includes a holding area, a cutter device, a container manipulation device, a pharmaceutical receptacle, and a container receptacle. The holding area is sized to retain a plurality of containers in a holding position, wherein a plurality of pharmaceuticals are contained within each container of the plurality of containers. The cutter device includes a cutter head and is configured to cut through at least one wall of at least one container to separate at least a first portion of the at least one container of the plurality of containers from a second portion of the at least one container when the at least one container is in a cutter position. The container manipulation includes a gripper device and is configured to move the at least one container between at least the holding position and the cutter position within the container disassembly workspace. The pharmaceutical receptacle is sized to receive the plurality of pharmaceuticals, wherein the plurality of pharmaceuticals are received from the at least one container after the first portion of the at least one container is separated from the second portion of the at least one container. The container receptacle defines an opening sized to receive the first portion of the at least one container and the second portion of the at least one container. The bulk containers are configured to receive a plurality of the plurality of pharmaceuticals from the container receptacle.

In another aspect, a container disassembly workstation defining a container disassembly workspace includes a holding area, a cutter device, a container manipulation device, a pharmaceutical receptacle, and a container receptacle. The holding area is configured to retain a plurality of containers in a holding position, wherein a plurality of pharmaceuticals are contained within each container of the plurality of containers. The cutter device is configured to separate at least a first portion of at least one container of the plurality of containers from a second portion of the at least one container in a cutting position of the cutter device. A container manipulation device is configured to move the at least one container within the container disassembly workspace such that the at least one container is moved between the holding position and the cutting position. The pharmaceutical receptacle is configured to receive the plurality of pharmaceuticals, wherein the plurality of pharmaceuticals are received from the at least one container after the first portion of the at least one container is separated from the second portion of the at least one container. The container receptacle is configured to receive the first portion of the at least one container and the second portion of the at least one container.

In yet another aspect, a method of disassembling a container includes scanning a holding area to determine if at least one container containing a plurality of pharmaceutical products is positioned in a holding position of the holding area of a container disassembly workstation. The method also includes capturing the at least one container with a container manipulation device. The method further includes moving the at least one container from the holding position to a cutter position proximate a cutter device. The method includes separating a first portion of the at least one container from a second portion of the at least one container using the cutter device. The method also includes transferring the plurality of pharmaceutical products from at least one of the first portion of the at least one container and the second portion of the at least one container to a pharmaceutical receptacle, wherein the pharmaceutical receptacle is sized to receive the plurality of pharmaceuticals. Finally, the method includes placing at least one of the first portion of the at least one container and the second portion of the at least one container in a container receptacle wherein the container receptacle defines an opening sized to receive the first portion of the at least one container and the second portion of the at least one container.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

In the drawings, reference numbers may be reused to identify similar and/or identical elements.

Corresponding reference characters indicate corresponding parts throughout the several views of the drawings.

DETAILED DESCRIPTION

Example systems and methods for processing a pharmacy order, for example, in a pharmacy, are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a pharmacy, and in some embodiments a high volume pharmacy. The prescription order may include more than one pharmaceutical, or prescription drug, for fulfillment. Each pharmaceutical in a prescription order is an order component of the prescription order. Generally, the order components are pill bottles, liquid bottles, blister packs, unit-of-use packs, injectable package, spray bottles, tubes, ampoules, drop counters, insulated boxes, child-resistant containers, or other packaging having a quantity of a pharmaceutical contained therein, the pharmaceuticals being required for the orders in varying and sometimes numerous quantities.

Figure 1:
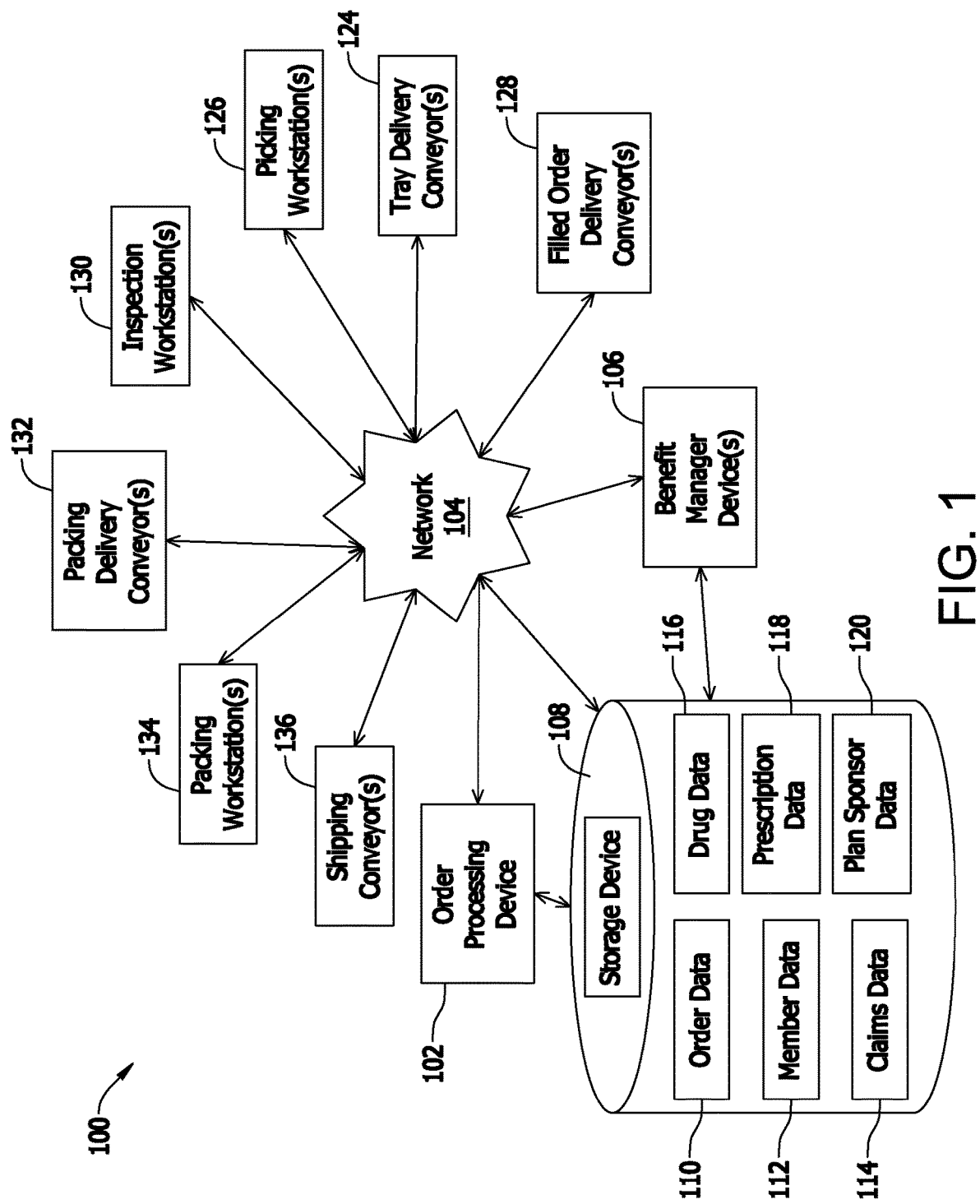
FIG. 1 is a block diagram of an example implementation of a pharmacy order processing system, according to an example embodiment.

FIG. 1 is a block diagram of an example implementation of a prescription order processing system 100 for a specialty pharmacy, according to an example embodiment. While the prescription order processing system 100 is generally described as being deployed in a specialty or a fulfillment center (e.g., a mail order pharmacy, a direct delivery pharmacy, etc., and the like), the prescription order processing system 100 and/or components thereof may otherwise be deployed (e.g., in a high volume pharmacy, etc.). A specialty pharmacy may be a pharmacy that is capable of filling prescriptions automatically, mechanically, manually, or a combination thereof. The prescription order processing system 100 may include a benefit manager device 106 and an order processing device 102 in communication with each other directly and/or over a network 104. The system may also include a storage device 108.

The benefit manager device 106 is a device operated by an entity that is at least partially responsible for creation and/or management of the pharmacy or drug benefit. While such entity operating the benefit manager device 106 is typically a pharmacy benefit manager (PBM), other entities may operate the benefit manager device 106 on behalf of themselves (i.e., the PBMs) or other entities. For example, the benefit manager device 106 may be operated by a health plan, a retail pharmacy chain, a drug wholesaler, a data analytics, or other type of software-related company, etc., or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, etc., and the like. The PBM may, in addition to its PBM operations, operate one or more than one pharmacies. The pharmacies may be retail pharmacies, mail order pharmacies, etc.

Some of the operations of the PBM that operates the benefit manager device 106 may include the following activities and processes. A member (or a person on behalf of the member) of a pharmacy benefit plan may obtain a prescription drug at a retail pharmacy location (e.g., a location of a physical store, etc.) from a pharmacist or a pharmacist technician. The member may also obtain the prescription drug through mail order drug delivery from a mail order pharmacy location, which may be the prescription order processing system 100. In some embodiments, the member may obtain the prescription drug directly or indirectly through the use of a machine, such as a kiosk, vending unit, mobile electronic device, or a different type of mechanical, electrical, electronic communication device and/or computing device. Such a machine may be filled with the prescription drug in prescription packaging, which may include multiple prescription components, by the prescription order processing system 100. The pharmacy benefit plan is administered by or through the benefit manager device 106.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, etc., or the like. In some instances, an employer of the member may directly or indirectly fund or reimburse the member for the copayments.

The amount of the copayment required by the member may vary with different pharmacy benefit plans having different plan sponsors or clients and/or for different prescription drugs. The member's copayment may be a flat copayment (e.g., $10, etc.), co-insurance (e.g., 10%, etc.), and/or a deductible (e.g., for first $500 of annual prescription drug expense, etc.) for certain prescription drugs, certain types and/or classes of prescription drugs, and/or all prescription drugs. The copayment may be stored in the storage device 108 or determined by the benefit manager device 106.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels used for the prescription drug to be received. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM, e.g., the benefit manager device, may perform certain adjudication operations including verifying eligibility for the member, identifying/reviewing an applicable formulary for the member to determine any appropriate copayment, coinsurance, and deductible for the prescription drug, and performing a drug utilization review (DUR) on the member. Further, the PBM may provide a response to the pharmacy, e.g., the pharmacy prescription order processing system 100, following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However in some instances, these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on types of pharmacy network in which the pharmacy is included. In some embodiments, the amount may also be determined based on other factors. For example, if the member pays the pharmacy for the prescription drug without using the prescription or drug benefit provided by the PBM, the amount of money paid by the member may be higher than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored in the benefit manager device 106 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102-110 or in parallel to link the devices 102-110.

The order processing device 102 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The order processing device 102 may be utilized by the pharmacy to submit the claim to the PBM for adjudication.

Additionally, in some embodiments, the order processing device 102 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager device 106 may track prescription drug fulfillment and/or other information for patients that are not members or have not identified themselves as members, at the time (or in conjunction with the time) in which they seek to have a prescription filled at a pharmacy.

The order processing device 102 may receive information regarding filling prescriptions and may direct an order component to one or more devices of the prescription order processing system 100 at a pharmacy. The order processing device 102 may fulfill, dispense, aggregate, and/or pack the order components of the prescription drugs in accordance with one or more prescription orders directed by the prescription order processing system 100. The order processing device 102 may be deployed in the prescription order processing system 100, or may otherwise be used.

In general, the order processing device 102 is a device located within or otherwise associated with the pharmacy to enable fulfillment of a prescription and dispensing prescription drugs. In some embodiments, the order processing device 102 may be an external device separate from the pharmacy and may communicate with other devices located within the pharmacy.

For example, the external order processing device 102 may communicate with an internal order processing device 102 and/or other devices located within the prescription order processing system 100. In some embodiments, the external order processing device 102 may have limited functionality (e.g., as operated by a patient requesting fulfillment of a prescription drug), while the internal order processing device 102 may have greater functionality (e.g., as operated by a pharmacist).

The order processing device 102 may track the prescription order as it is fulfilled by the prescription order processing system 100. The prescription order may include one or more than one prescription drugs to be filled by the pharmacy. The order processing device 102 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 102 may also track and/or schedule literature or paperwork associated with each prescription order or multiple prescription orders that are being shipped together.

The order processing device 102 may include circuitry, a processor, a memory to store data and instructions, and communication functionality. The order processing device 102 is dedicated to performing processes, methods and/or instructions described herein. Other types of electronic devices specifically configured to implement with the processes, methods and/or instructions described herein may also be used.

In some embodiments, at least some functionalities of the order processing device 102 may be included in the benefit manager device 106. The order processing device 102 may be in a client-server relationship with the benefit manager device 106, in a peer-to-peer relationship with the benefit manager device 106, or in a different type of relationship with the benefit manager device 106. The order processing device 102 and/or the benefit manager device 106 may communicate directly (e.g., by utilizing a local storage, etc.) and/or through the network 104 (e.g., by utilizing a cloud configuration or software as a service. etc.) with the storage device 108.

The storage device 108 may include: a non-transitory storage (e.g., memory, hard disk, CD-ROM, etc.) in communication with the benefit manager device 106, and/or the order processing device 102 directly and/or over the network 104. The non-transitory storage may store order data 110, member data 112, claims data 114, drug data 116, prescription data 118, and/or plan sponsor data 120. Further, the prescription order processing system 100 includes additional devices, including at least one container disassembly workstation 125, tray delivery conveyors 124, picking workstations 126, inspection workstations 130, packing delivery conveyors 132, packing workstations 134, and shipping conveyors 136, each additional device able to communicate with each other directly or over the network 104.

The order data 110 may be related to a prescription order. The order data may include type of the prescription drug (e.g., drug name and strength, etc.) and quantity of the prescription drug, etc. The order data 110 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high volume fulfillment center to fulfill a pharmacy order.

In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the prescription container (e.g., a prescription bottle and sealing lid, prescription packaging and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to transport prescriptions within the pharmacy may also be stored as order data 110.

The member data 112 includes information regarding the members associated with the PBM. The information stored as member data 112 may include personal information, personal health information, protected health information, and the like. Examples of the member data 112 include name, address, telephone number, e-mail address, prescription drug history, etc., and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, (e.g., the high volume fulfillment center, etc.), to obtain information utilized for fulfillment and shipping of prescription orders. In some embodiments, an external order processing device 102 operated by or on behalf of a member may have access to at least a portion of the member data 112 for review, verification, etc., or other purposes.

In some embodiments, the member data 112 may include information for persons who are patients of the pharmacy but are not members in the pharmacy benefit plan being provided by the PBM. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, GPI number, medication class, the cost of the prescription drug provided under the drug benefit program, the copay/coinsurance amount, rebate information, and/or member eligibility, etc. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member, etc.).

The drug data 116 may include drug name (e.g., technical name and/or common name, etc.), other names by which the drug is known by, active ingredients, an image of the drug (e.g., in pill form, etc.), and the like. The drug data 116 may include information associated with a single medication or multiple medications.

The prescription data 118 may include information regarding prescriptions that may be issued by prescribers on behalf of patients, who may be members of the pharmacy benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data 112, claims data 114, drug data 116, and/or prescription data 118.

The plan sponsor data 120 includes information regarding the plan sponsors of the PBM. Examples of the plan sponsor data 120 include company name, company address, contact name, contact telephone number, contact e-mail address, etc., and the like.

Figure 2:
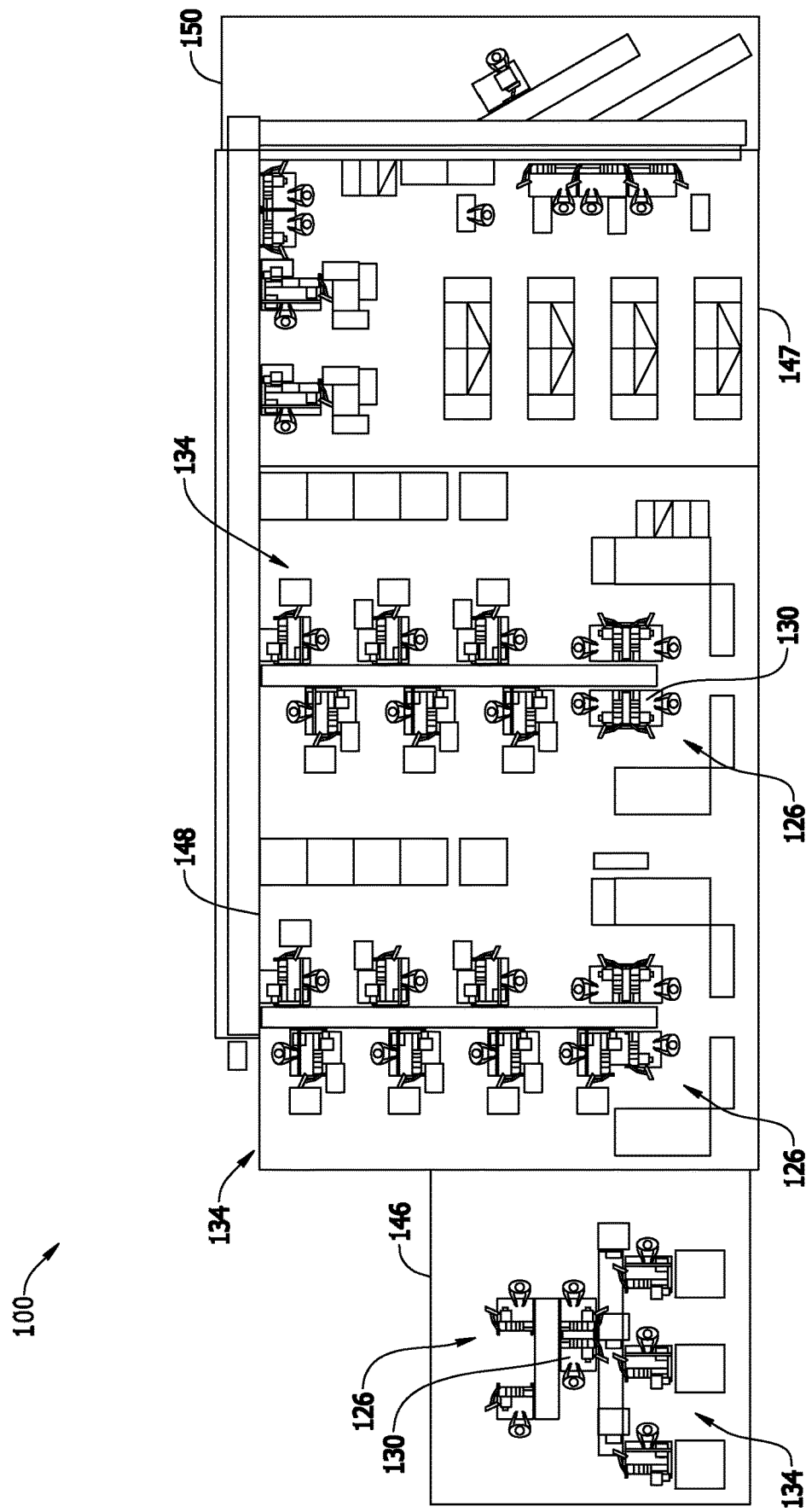
FIG. 2 is a plan view of a layout of the pharmacy order processing system shown in FIG. 1 according to an example embodiment.

FIG. 2 is a plan view of a layout of the prescription order processing system 100. The prescription order processing system 100 is configured to rapidly process, using a plurality of operators 107 at a number of stations, pharmacy orders from receipt of an order to shipping a packed filled order.

In the example embodiment, prescription order processing system 100 includes an ambient conditions section 146, a refrigerated conditions section 148, an ATX section 147, and a shipping section 150. Each of the ambient conditions section 146 and the refrigerated conditions section 148 includes a plurality of picking workstations 126, a plurality of packing workstations 134, and at least one inspection workstation 130, each workstation assigned one operator 107. Additionally, the refrigerated conditions section 148 includes at least one container disassembly workstation 125 with one assigned operator 107. The ATX section 147 includes two packing workstations 134 and a pair of quality assurance workstations 135. In some embodiments, prescription order processing system 100 may include as many types and number of workstations and operators 107 as facilitates operation of the prescription order processing system 100. As will be understood by one of ordinary skill, the ambient conditions section 146 is maintained at substantially room temperature, and the refrigerated conditions section 148 includes portions that are maintained at a temperature that is less than the ambient temperature. In the example embodiment, refrigerated conditions section 148 includes a plurality of reach-in coolers that maintain internal temperatures of between approximately 36° F. and 46° F., and at least one walk-in freezer that maintains an internal temperature of between approximately −14° F. and 14° F. In the example embodiment, each cooler and freezer includes a temperature alarm that sounds if a given temperature range is not met within a respective cooler or freezer for a 15 minute period.

In this embodiment, prescription order processing system 100 includes a plurality of ambient conveyors 137 and a plurality of conveyor assemblies 138. The ambient section 146 includes two ambient conveyors 137. One ambient conveyor 137 extends between the ambient picking workstations 126 and is positioned adjacent to the ambient inspection workstation 130. The second ambient conveyor 137 extends between the ambient packing workstations 134 and is positioned adjacent to the ambient inspection workstation 130 opposite to the first ambient conveyor 137. The refrigerated section 148 includes two conveyor assemblies 138 and a shipping conveyor 136. The first of the conveyor assemblies 138 extends from a first group of refrigerated picking workstations 126 through a first group refrigerated packing workstations 134 to an intersection with the shipping conveyor 136. The second of the conveyor assemblies 138 extends from a second group of refrigerated picking workstations 126, past a refrigerated inspection workstation 130, and through a second group of refrigerated packing workstations 134 to an intersection with the shipping conveyor 136. The shipping conveyor 136 extends from intersections with each of the conveyor assemblies 138 to the shipping section 150.

Figure 3:
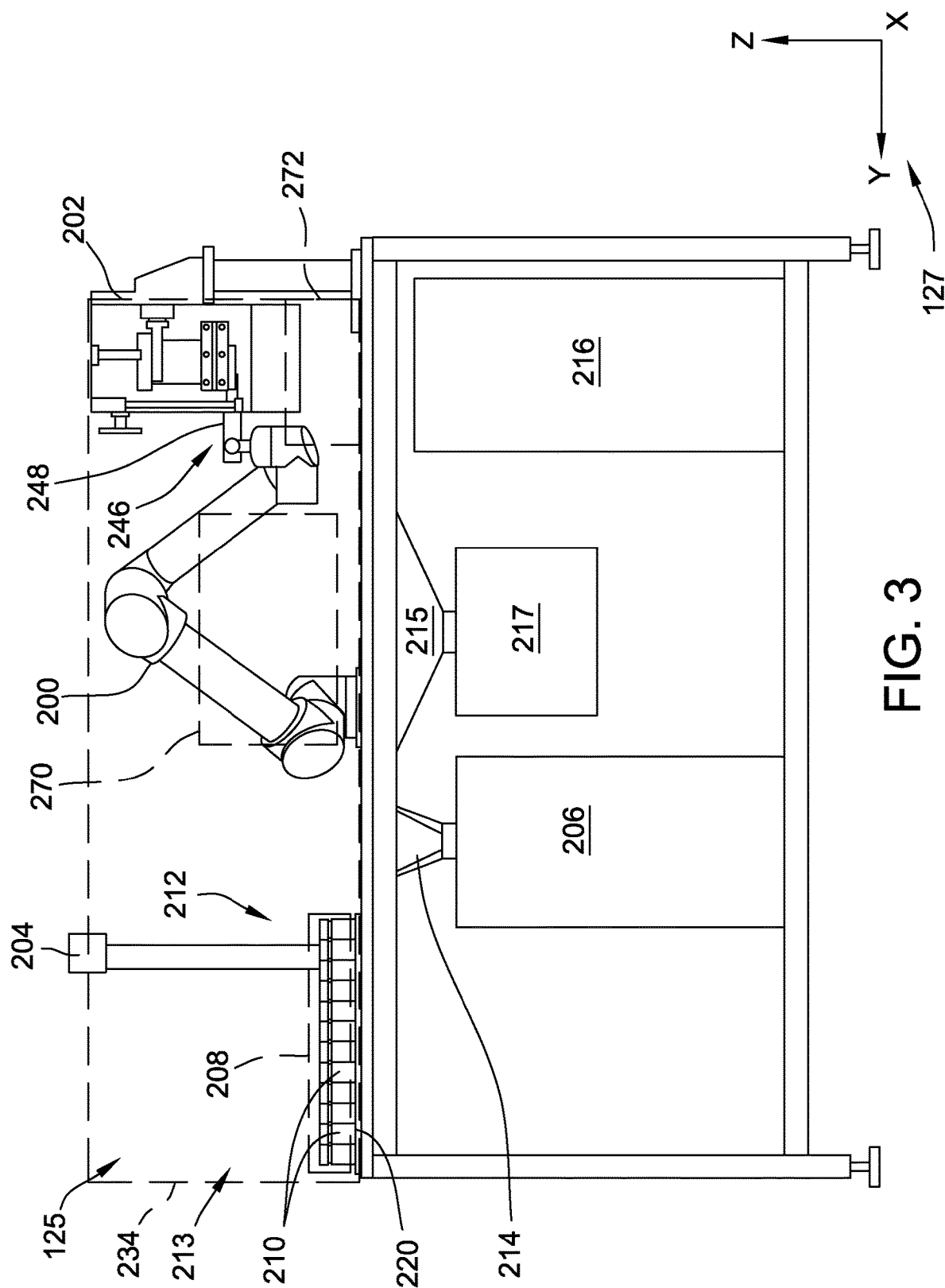
FIG. 3 is a front view of a container disassembly workstation for use with the system shown in FIG. 1 according to an example embodiment.

FIG. 3 is a front view of a container disassembly workstation 125 for use with the prescription order processing system 100 (shown in FIG. 1). A coordinate system 127 includes an X-axis, a Y-axis, and a Z-axis. In this embodiment, the container disassembly workstation 125 is configured to facilitate "bulking-up" of pharmaceuticals for filling orders in the prescription order processing system 100. More specifically, container disassembly workstation 125 includes a container manipulation device 200, a cutter device 202, and a scanner device 204, each device configured to cooperate with each other device to facilitate removing a plurality of pharmaceuticals contained within a plurality of containers for transferring to a bulk container 206. In the example embodiment, the bulk container is a one gallon container. The bulk containers 206 are transported to a central location within the prescription order processing system 100 to facilitate further distribution of the pharmaceuticals.

The container disassembly workstation 125 includes a holding area 208 configured to retain a plurality of the containers 210 in a holding position 212 defined therein, a pharmaceutical receptacle 214 configured to receive pharmaceuticals, a dust receptacle 215 configured to receive pharmaceutical dust, a container receptacle 216 configured to receive at least a portion of the containers 210, a vacuum system 217, and a container receptacle bin 218. In this embodiment, the holding area 208 includes a tray 220 including a plurality of holes defined therein, each hole configured to receive one of the containers 210. In an additional embodiment, the pharmaceutical receptacle 214 includes a door configured to inhibit pharmaceuticals from entering the pharmaceutical receptacle 214 until the door is in an open position. In some embodiments, the holding area 208 is configured to receive a crate, pallet or other type of container retaining component that is pre-loaded with the containers 210.

Figure 4:
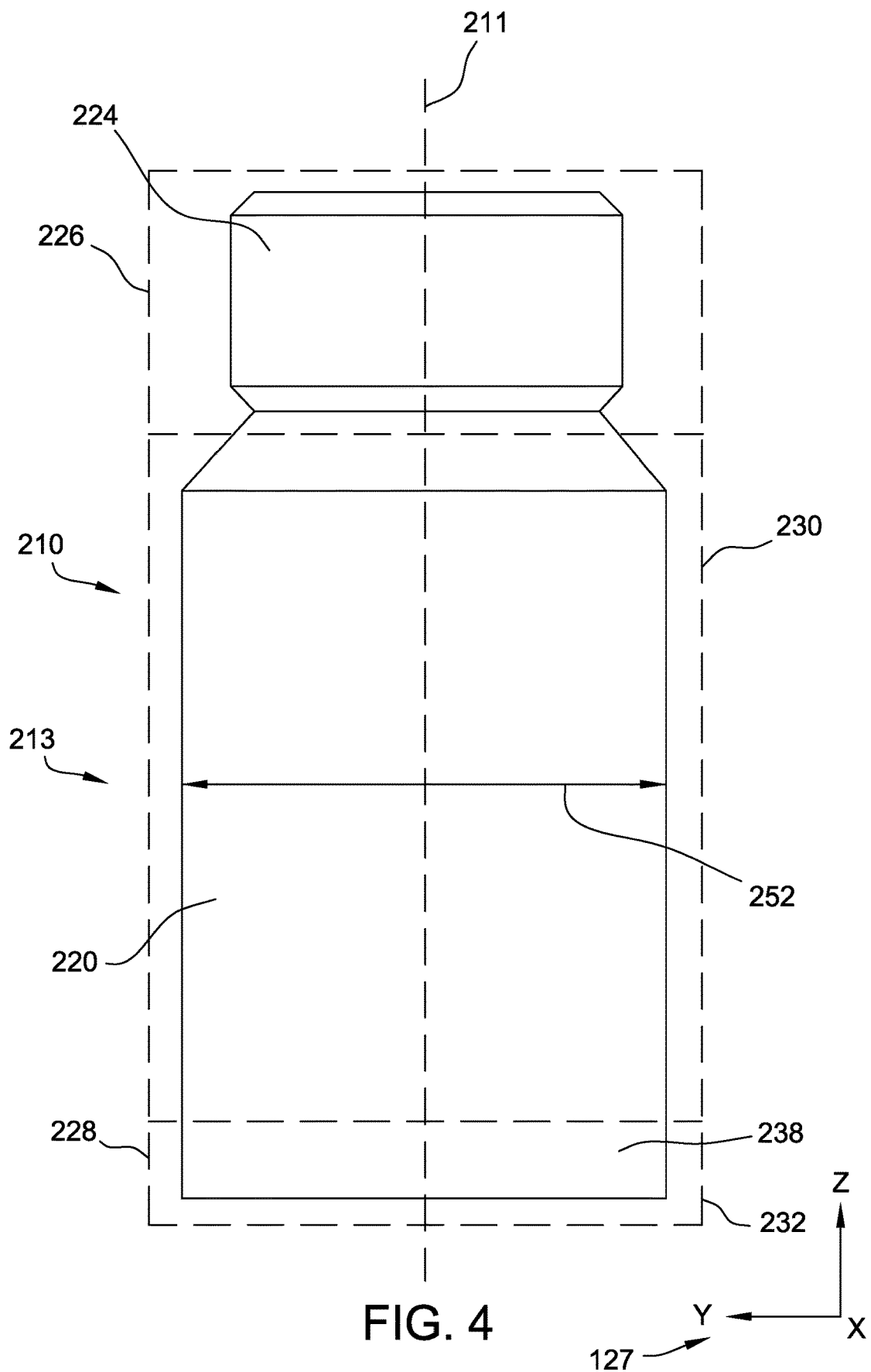
FIG. 4 is a front view of a container that may be used with the container disassembly workstation shown in FIG. 3 according to an example embodiment.

In this embodiment, the containers 210 are cylindrical hollow bottles having a body 222 and a lid 224. The body 222 includes a top 226 and a base 228, the top 226 being threaded to receive the lid 224 to facilitate retaining a plurality of pharmaceuticals within the container 210. A first portion 230 of the container 210 and a second portion 232 of the container 210 are defined as illustrated in FIG. 4. In this embodiment, the containers 210 are fabricated from a high-density polyethylene (HDPE) material. In some embodiments, the containers 210 are fabricated from at least one of polyethylene terephthalate (PET), #2 plastic, and #5 plastic. In additional embodiments, the containers 210 may have any shape and configuration that facilitates operation of prescription order processing system 100 as defined herein.

The scanner device 204 is coupled to container disassembly workstation 125 and extends along the Z-direction above the holding area 208. In this embodiment, the scanner device 204 is a laser proximity sensor and is configured to determine if at least one container 210 is positioned in the holding position 212, wherein a container 210 is in the holding position 212 when the container 210 is oriented within the holding area 208 such that the base 228 is positioned against the container disassembly workstation 125. In some embodiments, the scanner device 204 may be one of an optical proximity sensor, an ultrasonic sensor, and a capacitive proximity sensor. Additionally, in this embodiment, the scanner device 204 is configured to determine a height, location, and orientation of the containers 210 in the holding area 208. In additional embodiments, the scanner device 204 includes an array of scanner devices 204 further configured to determine the type of the containers 210.

The container manipulation device 200 is configured to move at least one of the containers 210 along at least one of the X-direction, the Y-direction, and the Z-direction within a container disassembly workspace 234 defined by the container disassembly workstation 125. More specifically, the container manipulation device 200 is a collaborative robot configured to move the container 210 between the holding position 212, a cutter position 236, an emptying position 270, and a discard position 272 to complete one cycle of the container disassembly workstation 125. In additional embodiments, the container manipulation device 200 is at least one of a selective-compliance-articulated robot arm, a six-axis robot, a cylindrical robot, a delta robot, a polar coordinate robot, a vertically articulated robot, and a Cartesian coordinate robot. In some embodiments, the container manipulation device 200 is configured to move more than one container 210 during each cycle of the container disassembly workstation.

In this embodiment, the container manipulation device 200 is adapted to facilitate the operator 107 working within the container disassembly workspace 234 without the container manipulation device 200 being guarded from interaction with the operators 107. In some embodiments, the container disassembly workspace 234 is guarded from the operators 107 by a guard configured to inhibit the operators 107 from interacting with the container manipulation device 200 while the container manipulation device 200 is operating. In some other embodiments, the container disassembly workspace 234 is guarded from the operators 107 at least partially by a sensor configured to detect entry of any portion of an operator 107 into workspace 234 and to cause at least the container manipulation device 200 to discontinue operation and movement.

Figure 5:
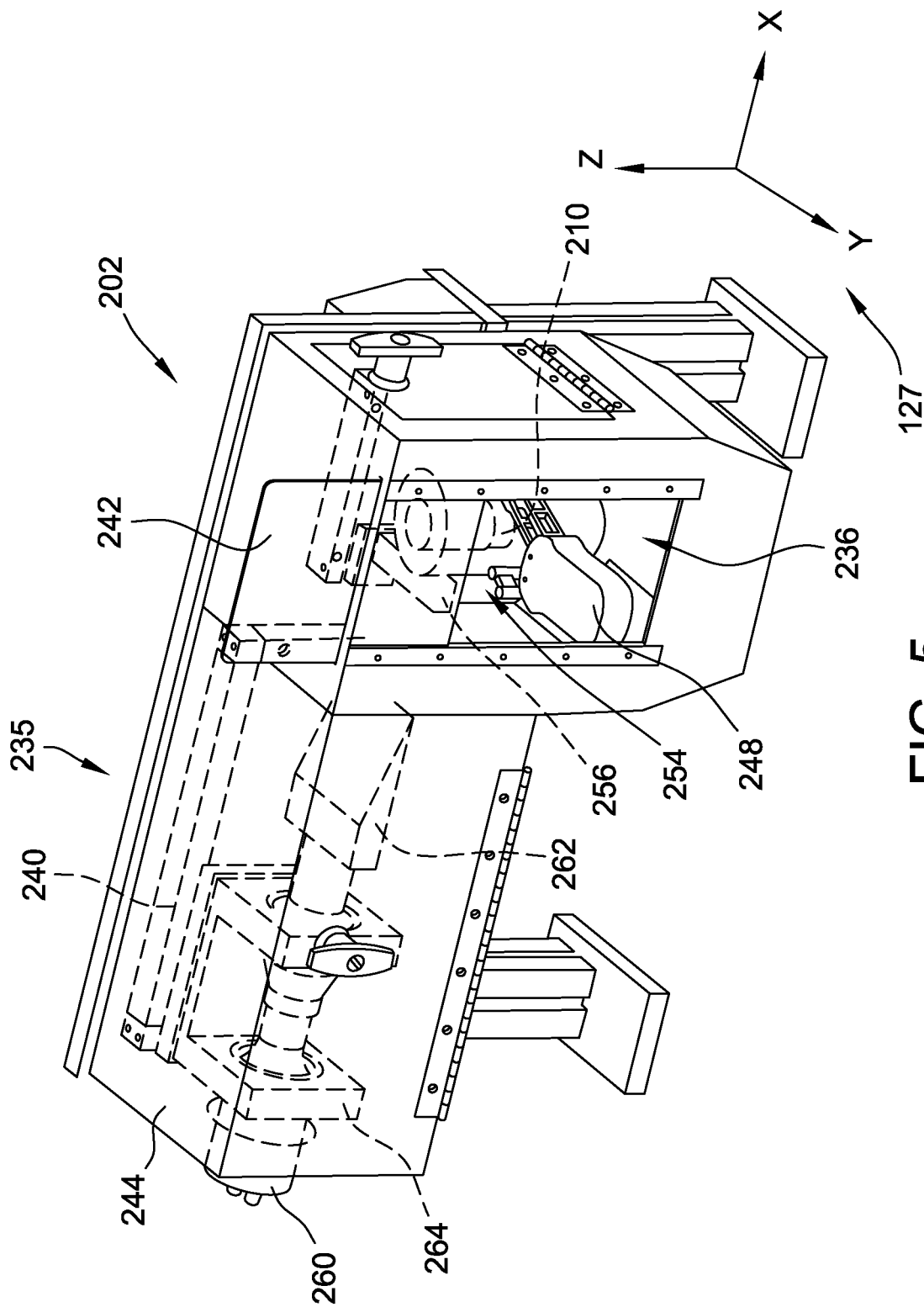
FIG. 5 is a perspective view of a cutter device for use with the container disassembly workstation shown in FIG. 3 illustrated in a non-cutting position according to an example embodiment.
Figure 6:
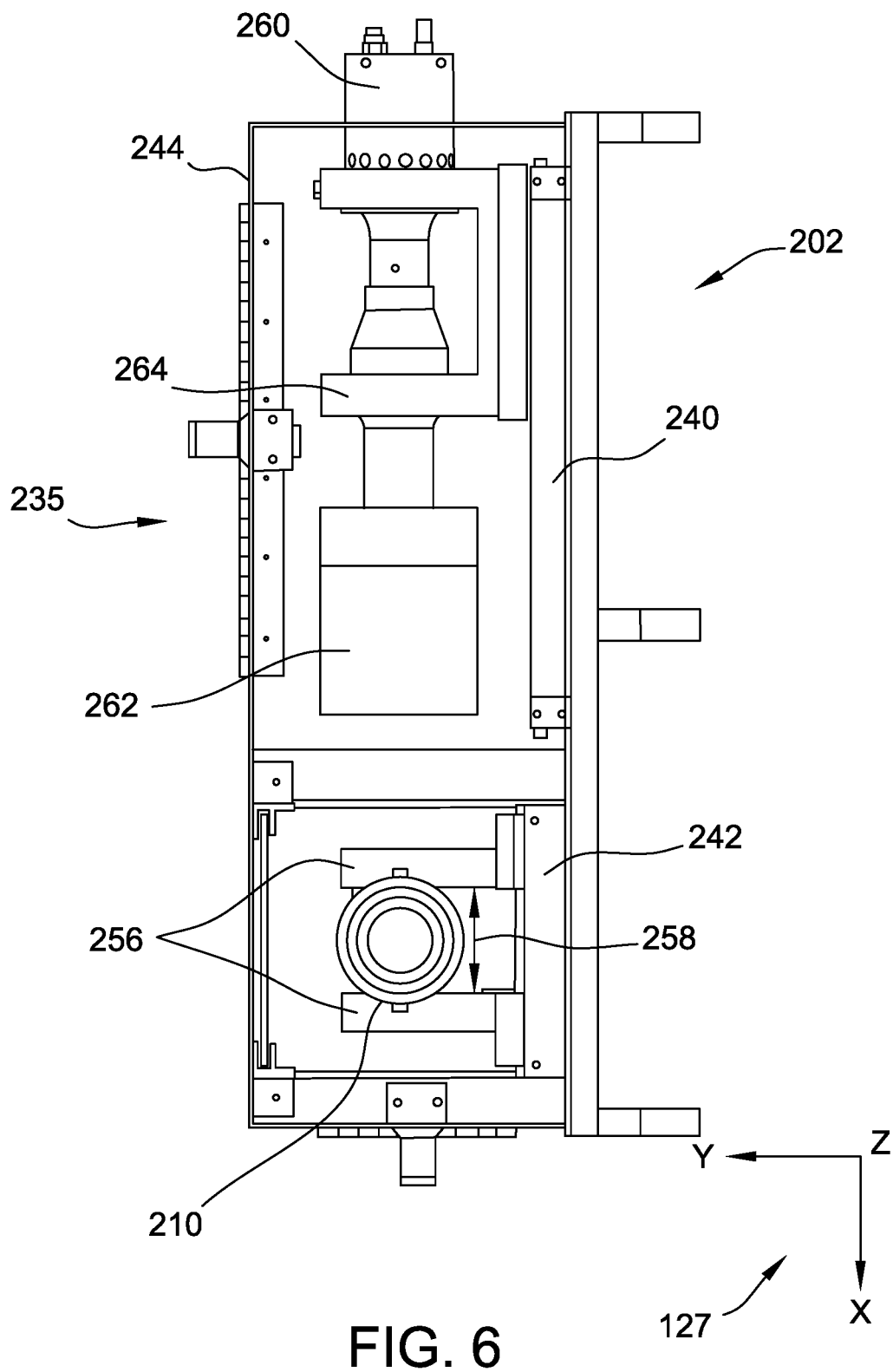
FIG. 6 is a plan view of the cutter device shown in FIG. 5 according to an example embodiment.

FIG. 4 is a front view of the container 210 that may be used with the container disassembly workstation 125 (shown in FIG. 3). FIG. 5 is a perspective view of the cutter device 202 for use with the container disassembly workstation 125 (shown in FIG. 3) illustrated in a non-cutting position 235. FIG. 6 is a plan view of the cutter device 202 (shown in FIG. 5). The cutter device 202 is configured to separate at least a first portion 230 of at least one of the containers 210 from a second portion 232 of the container 210. In this embodiment, the cutter device 202 is an ultrasonic cutter configured to cut through walls of a bottom portion 238 of the container 210 when the container 210 is in the cutter position 236 and includes a cutting force device 240 and a holder device 242 substantially surrounded by a plurality of guards 244. The plurality of guards 244 facilitate reducing the operators 107 exposure to cutter device 202 and debris created during the cutting operation. In this embodiment, the plurality of guards 244 substantially surrounding the cutter device 202 are oriented and positioned to facilitate directing at least one of the first portion 230 and the second portion 232 of the container 210 to the container receptacle 216 following the cutting operation. In additional embodiments, the cutter device 202 may be at least one of a rotary cutter, a rigid blade, and a thermal cutter.

In this embodiment, a working end 246 of the container manipulation device 200 includes a gripper device 248 configured to grip the first portion 230 of the container 210 in a first, upright orientation 213 at the holding position 212. More specifically, the gripper device 248 is configured to grip the container 210 such that a container longitudinal axis 211 is substantially aligned with the Z-direction and the lid 224 is vertically higher with respect to the Z-direction than the second portion 232 when the container 210 is in the first orientation 213. The gripper device 248 is a multiple-linkage two finger gripper device and is configured to grip containers 210 having a predetermined range of outer diameters 252. In this embodiment, the gripper device 248 is configured to grip the container 210 around the lid 224, the lid having an outer diameter 252 in a range of one half inch to five inches, and the container 210 having a total container weight of less than 3 pounds. In some embodiments, the gripper device 248 may grip the container 210 along any portion of the container 210 that facilitates operation of the container disassembly workstation 125 as described herein. In additional embodiments, gripper device 248 may be at least one of a three-finger gripper device, a multiple finger gripper device, or any other type of gripper device configured to grip and retain at least one container 210.

The container manipulation device 200 is also configured to then move the at least one container 210 from the holding position 212 in the first orientation 213 to the cutter position 236, proximate the cutter device 202. The container manipulation device 200 is further configured to then orient the at least one container 210 in a second, upside-down orientation 254 at the cutter position 236. The holder device 242 is configured to engage the container 210 at the cutter position 236 and to stabilize the container 210 during operation of the cutter device 202. In this embodiment, the holder device 242 includes two arms 256 movably coupled to the holder device 242 such that the arms 256 are able to move along the X-direction in order to vary an arm gap 258 to facilitate releasably retaining the containers 210 having outer diameters 252 within a specified range. In this embodiment, at closing spring (not shown) biases the arms 256 towards each other. In additional embodiments, the arms 256 may be biased towards each other using any component that facilitates retention of the containers 210 by the holder device 242 during operation of the cutter device 202.

Figure 7:
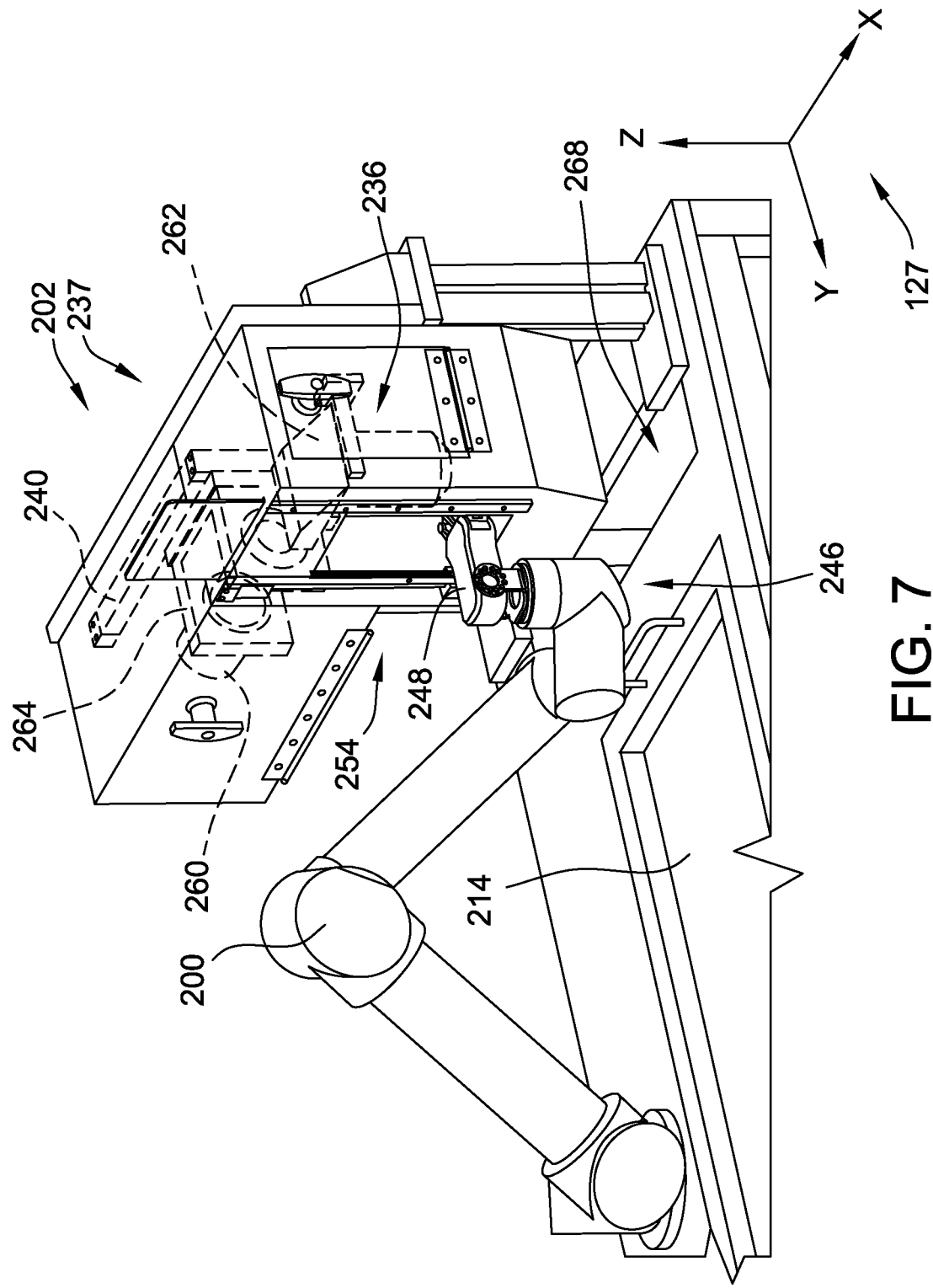
FIG. 7 is a perspective of the cutter device shown in FIG. 5 illustrated in a cutting position and illustrating a container manipulation device according to an example embodiment.
Figure 8:
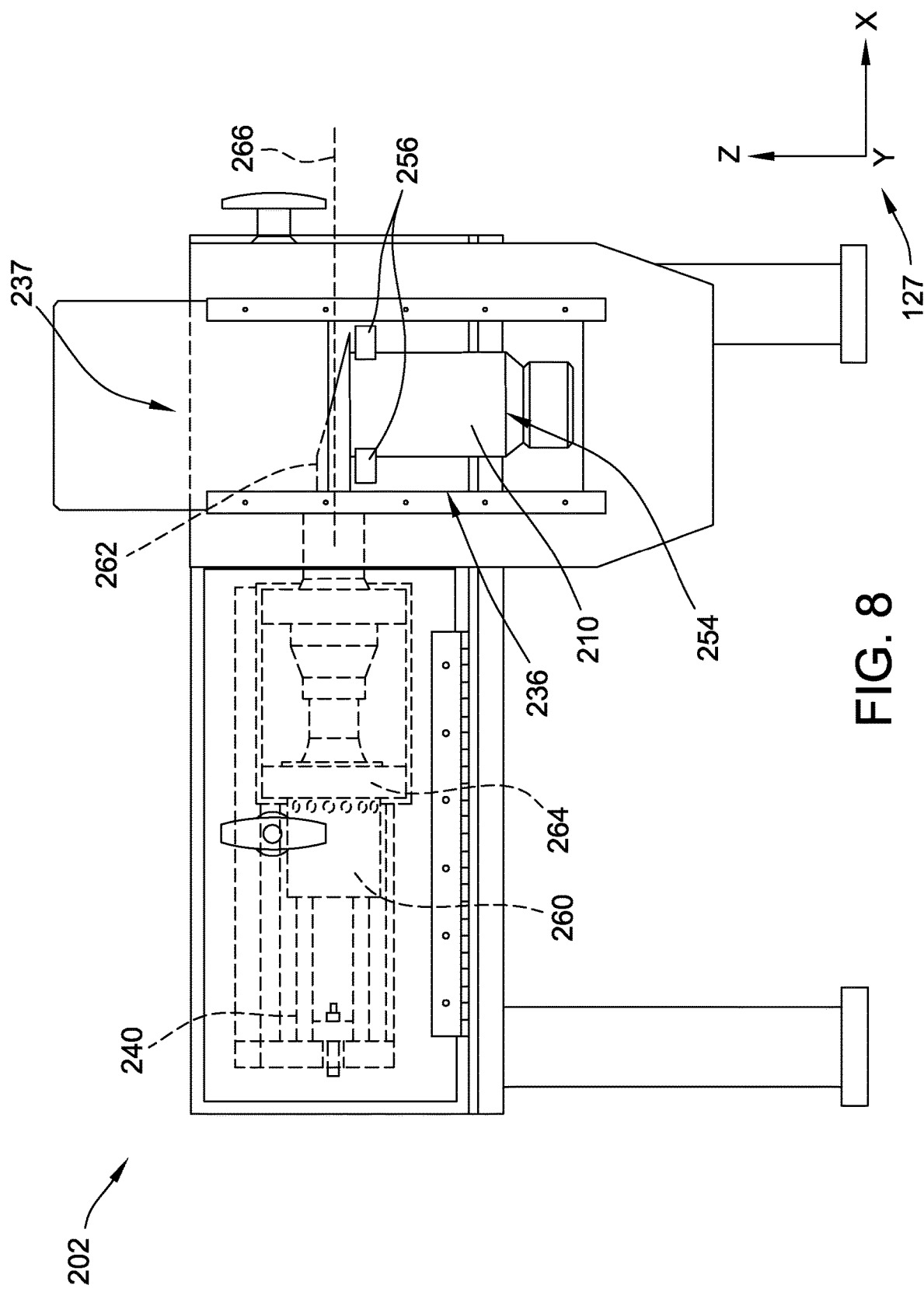
FIG. 8 is a front view of the cutter device shown in FIG. 7 according to an example embodiment.

FIG. 7 is a perspective of the cutter device 202 (shown in FIG. 5) illustrated in the cutting position 237. FIG. 8 is a front view of the cutter device 202 (shown in FIG. 7). In this embodiment, the cutter device 202 is slideably coupled to a cutting force device 240. The cutting force device is configured to bias the cutter device 202 along a cutter axis 266 towards the cutting position 237 such that the cutting force device 240 generates a cutting force between the cutter device 202 and the walls of the container 210 when the container 210 is in the cutter position 236. The cutting force device 240 is configured to generate the cutting force until the cutter device 202 has cut through the walls of the container 210 and caused the first portion 230 to be separated from the second portion 232 of the container 210.

In this embodiment, the cutter device 202 includes a cutter motor 260 and a cutter head 262 mounted within a resonant mount 264 coupled to the cutting force device 240. The cutter head 262 is a carbide cutter head 262. In some embodiments, the cutter head 262 may be fabricated from any material that facilitates separation of the first portion 230 from the second portion 232. The cutter motor 260 is configured to cause the cutter head 262 to oscillate along the cutter axis 266 at a frequency of thirty kilohertz (kHz). In additional embodiments, the cutter head 262 may be caused to oscillate at a frequency in a range of twenty to fifty kHz. The high-frequency oscillations of the cutter head 262 facilitate rapid and precise separation of the first portion 230 from the second portion 232 of the container 210, resulting in an opening to an inner cavity of the container 210.

After the first portion 230 has been separated from the second portion 232 of the container 210, a discard opening 268 receives the second portion 232 and the container manipulation device 200 is configured to move the first portion 230 from the cutter position 236 to an emptying position 270. In this embodiment, the emptying position 270 is defined above the pharmaceutical receptacle 214 along the Z-direction. The container manipulation device 200 orients the container 210 in the first orientation 213 and the plurality of pharmaceuticals are released from the inner cavity of the container 210 to the pharmaceutical receptacle 214. In this embodiment, the container manipulation device 200 is configured to move to a plurality of positions along an XY plane within an area defined by the emptying position 270 such that orienting the container 210 in the first orientation 213 causes the pharmaceuticals to fall onto a different portion of the pharmaceutical receptacle 214 than the pharmaceuticals deposited on the pharmaceutical receptacle 214 during the previous cycle of the container disassembly workstation 125. Additional packing materials such as cotton buffers and desiccants may be stored within the internal cavity with the pharmaceuticals and the operator 107 of the container disassembly workstation 125 may be required to separate the packing materials from the pharmaceuticals within the pharmaceutical receptacle 214.

In this embodiment, after the pharmaceuticals have been emptied from the first portion 230, the container manipulation device 200 is configured to move the first portion 230 from the emptying position 270 to a discard position 272. In this embodiment, the discard position 272 is defined above the discard opening 268 along the Z-direction. The container manipulation device 200 orients the first portion 230 above the discard opening 268 and releases the first portion 230 through the discard opening 268 to the container receptacle 216. In some embodiments, the container manipulation device 200 is configured to move the pharmaceuticals that have been emptied onto the pharmaceutical receptacle 214 from the pharmaceutical receptacle 214 to a bulk container 206. The above-described cycle continues until none of the containers 210 are present in the holding area 208, or until the container disassembly workstation 125 is otherwise caused to stop.

Figure 9A:
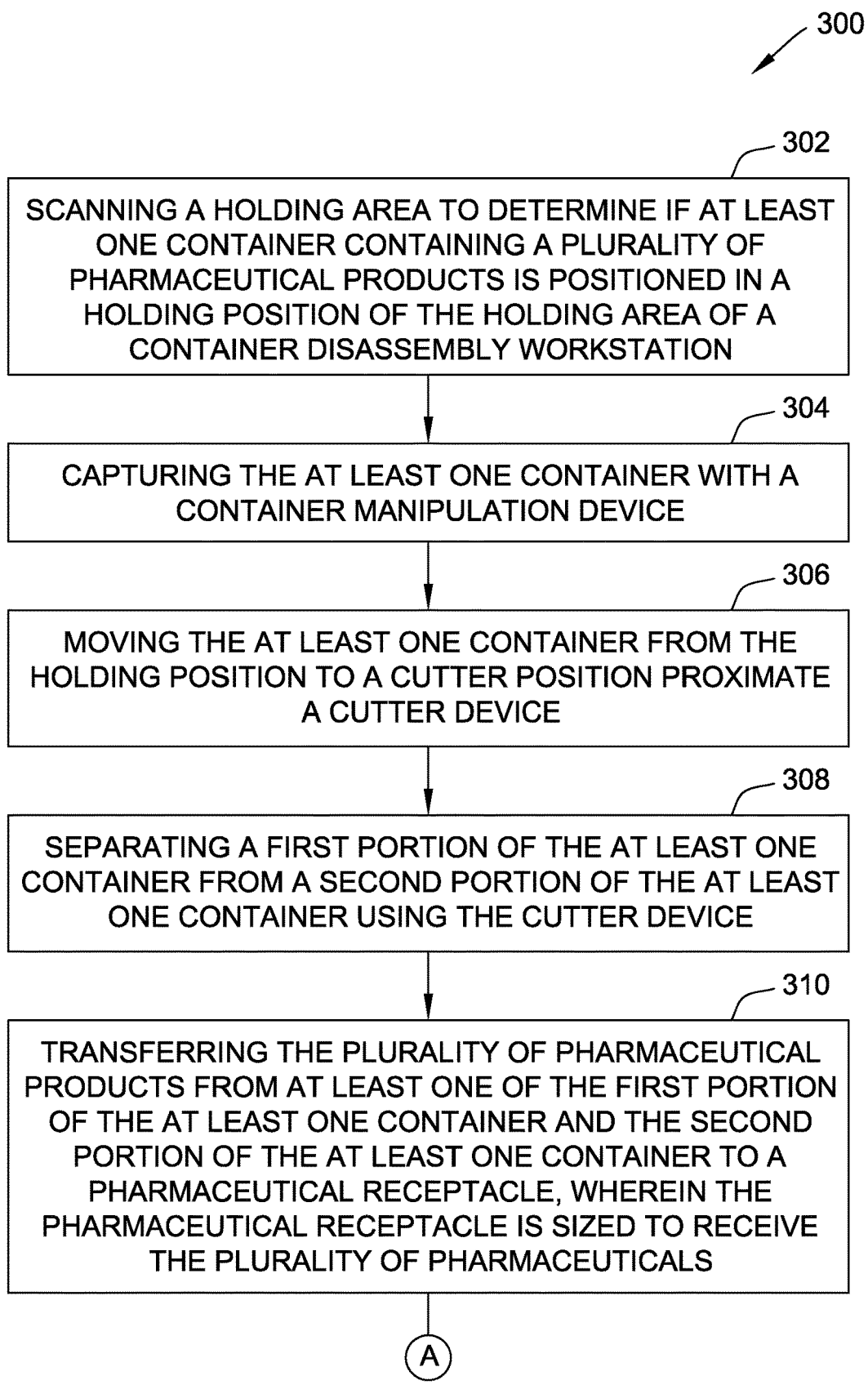
FIGS. 9A and 9B are an example process flow illustrating a method for processing pharmacy orders, according to an example embodiment.
Figure 9B:

FIG. 9 is an example process flow illustrating a method 300 for disassembling a container 210 that contains pharmaceuticals. Method 300 includes scanning 302 a holding area 208 to determine if at least one container 210 containing a plurality of pharmaceutical products is positioned in a holding position 212 of the holding area 208 of a container disassembly workstation 125. Method 300 also includes capturing 304 the at least one container 210 with a container manipulation device 200. Method 300 further includes moving 306 the at least one container 210 from the holding position 212 to a cutter position 236 proximate a cutter device 202. Method 300 includes separating 308 a first portion 230 of the at least one container 210 from a second portion 232 of the at least one container 210 using the cutter device 202. Method 300 includes transferring 310 the plurality of pharmaceutical products from at least one of the first portion 230 and the second portion 232 to a pharmaceutical receptacle 214, wherein the pharmaceutical receptacle 214 is configured to receive the plurality of pharmaceutical products. Finally, method 300 includes placing 312 at least one of the first portion 230 and the second portion 232 in a container receptacle 216, wherein the container receptacle 216 is configured to receive at least one of the first portion 230 of the at least one container 210 and the second portion 232 of the at least one container 210.

Embodiments of the methods and systems described herein achieve superior results as compared to prior methods and systems. For example, unlike known pharmaceutical unpacking and combining systems, the pharmaceutical container disassembly and pharmaceutical bulk packaging systems described herein are configured to operate with minimal operator input and interaction with the workstation. In particular, the container disassembly workstations described are operable such that a plurality of pharmaceutical containers may be disassembled, and the pharmaceuticals contained therein removed, with reduced operator input required as compared to known systems, enabling an operator to operate multiple container disassembly workstations simultaneously. As a result, specialty and custom pharmacies can be retrofitted with the container disassembly workstations, thereby increasing the safety and efficiency of existing specialty and custom pharmacies. These workstations can have container manipulation devices that do not require guarding incorporated into the workstation such that the operator is able to work in the same workspace as the container manipulation device, further improving safety and efficiency of the workstation. Further, unlike some known pharmaceutical unpacking and combining systems that depend on the operator to feed containers into the unpacking and combining system, the workstations described herein allow an operator to place containers in a designated holding area where a scanner scans the containers and provides their locations and container types to the container manipulation device for processing, further improving the efficiency of the system. Additionally, unlike some known pharmaceutical unpacking and combining systems, the workstations described herein do not require the operators to manually remove, cut, or open any portion of the container to release the pharmaceuticals, improving operator safety and system efficiency.

The term "based on" or using, as used herein, reflects an open-ended term that can reflect others elements beyond those explicitly recited. Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and sub-systems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

At least some portions of the present disclosure may be accomplished by using a robot. A robot can be a machine capable of carrying out a complex series of actions automatically. These complex series of actions may include picking up, orientating, positioning and/or releasing a prescription component, a pill, a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, may move location, have an articulated arm, have grasping structures that replicate fingers and do not damage containers, and the like.

Methods and systems for pharmacy order processing have been described. Although embodiments of the present disclosure have been described with reference to specific example embodiments, it will be evident that various modifications and changes may be made to these embodiments without departing from the broader spirit and scope of the embodiments of the disclosure. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The systems and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

Embodiments for pharmacy order processing are described above in detail. The systems and methods of operating such systems are not limited to the specific embodiments described herein, but rather, components of systems and/or steps of the methods may be utilized independently and separately from other components and/or steps described herein. For example, the methods may also be used in combination with other systems and environments and are not limited to the environments as described herein. Rather, the embodiments can be implemented and utilized in connection with many other applications.

In this specification and the claims, reference is made to a number of terms, which shall be defined to have the following meanings:

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

The term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, cd-roms, dvds, and any other digital source such as a network or the internet, as well as yet to be developed digital means, with the sole exception being a transitory, propagating signal.

The terms "software" and "firmware" are interchangeable, and include any computer program stored in memory for execution by devices that include, without limitation, mobile devices, clusters, personal computers, workstations, clients, and servers.

The term "computer" and related terms, e.g., "computing device", are not limited to integrated circuits referred to in the art as a computer, but broadly refers to a microcontroller, a microcomputer, a programmable logic controller (plc), an application specific integrated circuit, and other programmable circuits, and these terms are used interchangeably herein.

Computer systems are described, and such computer systems include a processor and a memory. However, any processor in a computer device referred to may also refer to one or more processors wherein the processor may be in one computing device or a plurality of computing devices acting in parallel, such as in a cloud computing environment. Additionally, any memory in a computer device referred to may also refer to one or more memories, wherein the memories may be in one computing device or a plurality of computing devices acting in parallel.

A processor may include any programmable system including systems using micro-controllers, reduced instruction set circuits (risc), application specific integrated circuits (asics), logic circuits, and any other circuit or processor capable of executing the functions described herein. The above examples are example only, and are thus not intended to limit in any way the definition and/or meaning of the term "processor." The term "database" may refer to either a body of data, a relational database management system (rdbms), or to both. A database may include any collection of data including hierarchical databases, relational databases, flat file databases, object-relational databases, object oriented databases, and any other structured collection of records or data that is stored in a computer system. The above are only examples, and thus are not intended to limit in any way the definition and/or meaning of the term database. Examples of rdbms's include, but are not limited to including, Oracle® Database, Mysql, IBM® Db2, Microsoft® Sql Server, Sybase®, and Postgresql. However, any database may be used that enables the systems and methods described herein. (oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In some embodiments, a computer program is embodied on a computer readable medium. In other embodiments, the system is executed on a single computer system, without requiring a connection to a server computer. In still other embodiments, the system is run in a Windows® environment (windows is a registered trademark of Microsoft corporation, Redmond, Wash.). In yet another embodiment, the system is run on a mainframe environment and a Unix® server environment (Unix is a registered trademark of x/open company limited located in reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The inventive subject matter may be represented in a variety of different embodiments of which there are many possible permutations. Although specific features of various embodiments of the invention may be shown in some drawings and not in others, this is for convenience only. In accordance with the principles of the invention, any feature of a drawing may be referenced and/or claimed in combination with any feature of any other drawing. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A pharmacy order processing system comprising:
   a container disassembly workstation defining a container disassembly workspace, the container disassembly workstation comprising:
   a holding area sized to retain a plurality of containers in a holding position, wherein a plurality of pharmaceuticals are contained within each container of the plurality of containers;
   a cutter device comprising a cutter head and adapted to cut through at least one wall of at least one container to separate at least a first portion of the at least one container of the plurality of containers from a second portion of the at least one container when the at least one container is in a cutter position;
   a container manipulation device including a gripper, the container manipulation device is configured to move the at least one container between at least the holding position and the cutter position within the container disassembly workspace, the container manipulation device further configured to move the first portion of the at least one container from the cutter position to an emptying position where the pharmaceuticals are removed from the first portion of the at least one container;
   a pharmaceutical receptacle sized to receive the plurality of pharmaceuticals, wherein the plurality of pharmaceuticals are received from the at least one container after the first portion of the at least one container is separated from the second portion of the at least one container and the first portion of the at least one container is moved to the emptying position by the container manipulation device; and
   a container receptacle defining an opening sized to receive the first portion of the at least one container and the second portion of the at least one container; and
   a bulk container area including a bulk container, the bulk container configured to receive a plurality of the plurality of pharmaceuticals from the container receptacle.

2. The pharmacy order processing system of claim 1, wherein the gripper is at least one of a multiple finger gripper device and a multiple-linkage gripper device, and wherein the gripper is configured to grip the at least one container having an outer diameter within a predetermined range of outer diameters.

3. The pharmacy order processing system of claim 1, further including a holder device configured to stabilize the at least one container during operation of the cutter device.

4. The pharmacy order processing system of claim 1, wherein the bulk container area includes a plurality of bulk containers, the bulk containers configured to receive the plurality of the plurality of pharmaceuticals from the container receptacle.

5. The pharmacy order processing system of claim 1, wherein the pharmaceutical receptacle and the container receptacle are fixed relative to one another in the container disassembly workspace.

6. The pharmacy order processing system of claim 1, wherein the container manipulation device is one of a collaborative robot adapted to allow an operator to occupy the container disassembly workspace, a six-axis robot, a selective-compliance-articulated robot arm, a cylindrical robot, a delta robot, a polar coordinate robot, a vertically articulated robot, and a Cartesian coordinate robot.

7. The pharmacy order processing system of claim 6, wherein the container manipulation device is further configured to:
   grip the first portion of the at least one container in a first, upright orientation at the holding position;
   move the at least one container from the holding position to the cutter position;
   orient the at least one container in a second, upside-down orientation at the cutter position; and
   orient the first portion of the at least one container in the first orientation at the emptying position.

8. The pharmacy order processing system of claim 1, wherein the cutter device is one of an ultrasonic cutter, a rotary cutter, and a thermal cutter.

9. The pharmacy order processing system of claim 8, wherein the cutter device includes a cutting force device, wherein the cutting force device is configured to generate a cutting force between the cutter device and the at least one container in the cutter position.

10. The pharmacy order processing system of claim 1, further including a scanner device configured to determine if at least one container is positioned in the holding position.

11. The pharmacy order processing system of claim 10, wherein the scanner device is one of a laser proximity sensor, an optical proximity sensor, an ultrasonic sensor, and a capacitive proximity sensor.

12. The pharmacy order processing system of claim 10, wherein the scanner device is an array of scanner devices further configured to determine if the at least one container is a first type of container.

13. The pharmacy order processing system of claim 10, wherein the scanner device is further configured to determine a height, a location, and an orientation of the at least one container in the holding area.

14. A container disassembly workstation defining a container disassembly workspace, the container disassembly workstation comprising:
   a holding area sized to retain a plurality of containers in a holding position, wherein a plurality of pharmaceuticals are contained within each container of the plurality of containers;
   a cutter device comprising a cutter head and configured to cut through at least one wall of at least one container to separate at least a first portion of the at least one container of the plurality of containers from a second portion of the at least one container when the at least one container is in a cutter position;
   a robotic arm comprising a gripper, the robotic arm configured to move the at least one container from at least the holding position to another position within the container disassembly workspace, the robotic arm configured to rotate about at least a first axis and a second axis, the first and second axis being non-parallel with one another;
   a pharmaceutical receptacle sized to receive the plurality of pharmaceuticals, wherein the plurality of pharmaceuticals are received from the at least one container after the first portion of the at least one container is separated from the second portion of the at least one container; and
   a container receptacle defining an opening sized to receive at least one of the first portion of the at least one container and the second portion of the at least one container.

15. The workstation of claim 14, wherein the gripper is at least one of a two finger gripper device and a multiple-linkage three finger gripper device, and wherein the gripper is configured to grip the at least one container having an outer diameter within a predetermined range of outer diameters.

16. The workstation of claim 14, further including a holder device configured to stabilize the at least one container during operation of the cutter device.

17. The container disassembly workstation of claim 14, wherein the pharmaceutical receptacle and the container receptacle are fixed relative to one another in the container disassembly workspace.

18. The workstation of claim 14, wherein the robotic arm is a six-axis robotic arm.

19. The workstation of claim 18, wherein the robotic arm is further configured to:
   grip the first portion of the at least one container in a first, upright orientation at the holding position;
   move the at least one container from the holding position to the cutter position;
   orient the at least one container in a second, upside-down orientation at the cutter position;
   move the first portion of the at least one container from the cutter position to an emptying position where the pharmaceuticals are removed from the first portion of the at least one container; and
   orient the first portion of the at least one container in the first orientation at the emptying position.

20. The workstation of claim 14, wherein the cutter device is one of an ultrasonic cutter, a rotary cutter, a rigid blade, and a thermal cutter.

21. The workstation of claim 20, wherein the cutter device includes a cutting force device, wherein the cutting force device is configured to generate a cutting force between the cutter device and the at least one container in the cutter position.

22. The workstation of claim 14, further including a scanner device configured to determine if at least one container is positioned in the holding position.

23. The workstation of claim 22, wherein the scanner device is one of a laser proximity sensor, an optical proximity sensor, an ultrasonic sensor, and a capacitive proximity sensor.

24. The workstation of claim 22, wherein the scanner device is an array of scanner devices further configured to determine if the at least one container is a first type of container.

25. The workstation of claim 22, wherein the scanner device is further configured to determine a height, a location, and an orientation of the at least one container in the holding area.

26. A method of disassembling a container, the method including:
   scanning a holding area to determine if at least one container containing a plurality of pharmaceutical products is positioned in a holding position of the holding area of a container disassembly workstation;
   capturing the at least one container with a container manipulation device;
   moving the at least one container from the holding position to a cutter position proximate a cutter device with the container manipulation device;
   separating a first portion of the at least one container from a second portion of the at least one container using the cutter device;
   moving the first portion of the at least one container from the cutter position to an emptying position with the container manipulation device;
   transferring the plurality of pharmaceutical products from the first portion of the at least one container to a pharmaceutical receptacle at the emptying position, wherein the pharmaceutical receptacle is sized to receive the plurality of pharmaceuticals; and
   placing at least one of the first portion of the at least one container and the second portion of the at least one container in a container receptacle, wherein the container receptacle defines an opening sized to receive the first portion of the at least one container and the second portion of the at least one container.

27. The method of claim 26, wherein moving the at least one container from the holding area to a cutter device includes:
   gripping the first portion of the at least one container in a first, upright orientation at the holding position with the container manipulation device;
   moving the at least one container from the holding position to the cutter position with the container manipulation device; and
   orienting the at least one container in a second, upside-down orientation at the cutter position; and wherein moving the first portion of the at least one container from the cutter position to the emptying position with the container manipulation device includes:
orienting the first portion of the at least one container in the first orientation at the emptying position.

28. The method of claim 26, wherein scanning the holding area includes using a scanner device, wherein the scanner device is one of a laser proximity sensor, an optical proximity sensor, an ultrasonic sensor, and a capacitive proximity sensor, and wherein the scanner device is configured to determine a height, a location, and an orientation of the at least one container in the holding position.

29. The method of claim 26, wherein separating a first portion of the at least one container from a second portion of the at least one container includes using one of an ultrasonic cutter, a rotary cutter, and a thermal cutter.

30. The method of claim 26, wherein the pharmaceutical receptacle and the container receptacle are fixed relative to one another in a container disassembly workspace of the container disassembly workstation.

\* \* \* \* \*